United States Patent [19]

Wernli

[11] 4,087,385

[45] May 2, 1978

[54] PROCESS FOR MAKING A SILVER CATALYST FOR OXIDIZING ETHYLENE TO ETHYLENE OXIDE

[75] Inventor: Walter Lesley Wernli, Angleton, Tex.

[73] Assignee: The Dow Chemical Company, Midland, Mich.

[21] Appl. No.: 780,220

[22] Filed: Mar. 23, 1977

[51] Int. Cl.² .................. B01J 23/02; B01J 23/14; B01J 23/50; B01J 23/52

[52] U.S. Cl. ................................ 252/475; 252/476; 260/348.34

[58] Field of Search .............................. 252/475, 476

[56] References Cited

U.S. PATENT DOCUMENTS

| 3,702,259 | 11/1972 | Nielsen | 427/229 |
|---|---|---|---|
| 4,007,135 | 2/1977 | Hayden et al. | 252/476 X |

*Primary Examiner*—W. J. Shine
*Attorney, Agent, or Firm*—A. Cooper Ancona

[57] ABSTRACT

An improved method for the preparation of a silver catalyst in which a cyclic tetraamine is employed as a dispersing agent for the silver compound. Such catalysts are useful in the preparation of ethylene oxide by the direct oxidation of ethylene.

5 Claims, No Drawings

PROCESS FOR MAKING A SILVER CATALYST FOR OXIDIZING ETHYLENE TO ETHYLENE OXIDE

BACKGROUND OF THE INVENTION

It is known that the better silver catalysts for the vapor phase oxidation of ethylene to ethylene oxide are formed by depositing silver upon a suitable support or carrier. It is also known that the silver deposit in the best catalysts is in the form of extremely fine grains of silver. One method of obtaining such fine grains, or crystals, of silver is by employing a dispersing agent in the solution of the silver compound in which the catalyst support is to be impregnated.

To obtain such finely divided silver various methods have been suggested by the prior art. In U.S. Pat. No. 2,404,438 certain carboxylic acid salts of silver are taught as useful in preparing a finely divided particulate silver for a supported catalyst. Polymers of unsaturated carboxylic acids are employed in U.S. Pat. No. 3,758,418 for a similar purpose. More recently in U.S. Pat. No. 3,887,491 certain natural gums, e.g. karaya, are employed in the aqueous silver-containing solution.

Another group of compounds which act as dispersing agents has now been discovered which provides a catalyst which is much more selective while still maintaining, or even improving, the conversion obtained; a lower temperature is required to obtain the same results thus saving energy. One species of the generic compound employed is disclosed in U.S. Pat. No. 3,893,855. At Column 3, lines 1–15, structural formula "B" shows the 5,7,7,12,14,14-hexamethyl-1,4,8,11-tetraazacyclotetradecane employed in the examples of the present invention. These compounds are used to complex silver in coatings employed as photosensitive elements. The preparation of such compounds has been described in a paper by N. F. Curtis, Journal of the Chemical Society, 2644, 1964.

SUMMARY OF THE INVENTION

According to the present invention an improved silver catalyst is prepared by (1) impregnating a suitable support with a silver solution containing a cyclic tetraamine compound, (2) drying the support and finally (3) reducing the impregnated silver salt to silver metal.

DETAILED DESCRIPTION OF THE INVENTION

Generally, aqueous solutions are used to prepare the catalysts, i.e., solutions from which the silver salts and the cyclic tetraamine are impregnated onto the support. Glycols or alcohols may be employed to enhance the solubility of the amine in the aqueous solution.

The catalyst carriers or supports include, but are not necessarily limited to, fused alumina, zirconia, corundum, mullite, silicon carbide and carbon. Alumina is the preferred carrier, and most preferred is a spherical alumina having a surface area of 1 square meter or less per gram, a bulk density of 1.7 to 2.0 grams per cc, a packing density of 58 to 65 lbs. per cubic foot, and having 95 percent of the pore diameter in 4–70 micron range.

The physical shape of the catalyst can be small spheres ⅛ to ½-inch in diameter or small ringlets or any other convenient shaped particulate carrier. The preferred form is spherical.

The silver salt can be any soluble silver compound. Representative silver salts which can be used in solution are silver acetate, silver nitrate, silver lactate, silver fluoride and silver chlorate or perchlorate. The preferred salt is silver nitrate, because of its ready availability and relatively easy reduction to metallic silver in the presence of a reducing agent, conveniently hydrogen gas, lower hydrocarbon or CO, if such step is desired. The concentrations of the silver salt in solution can be adjusted to provide 2 to 25 percent by weight, and preferably 4 to 20 percent by weight, of silver on the carrier. A most preferred range is 10 to 18 percent since this is the range of silver concentration wherein the present process is of greatest advantage.

The cyclic tetraamines employed in the process of the present invention are generally selected from tetraazacycloalkanes having the formula

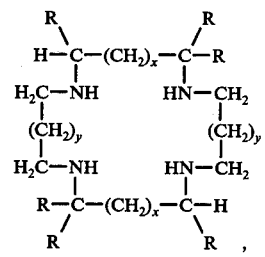

wherein $x$ and $y$ are independently selected integers of either 0 or 1 and R is methyl or ethyl. Depending upon the value of $x$ and $y$, the cyclic tetraamine compound can be methyl- or ethyl-substituted cyclododecanes, -cyclotetradecanes, or -cyclohexadecanes, i.e., including the carbons and nitrogens, the ring may contain 12, 14 or 16 atoms, which, of course, excludes hydrogen and alkyl substituents on the ring-forming atoms.

Especially preferred are 5,7,7,12,14,14-hexamethyl-1,4,8,11-tetraazacyclotetradecane and 5,7,7,12,14,14-hexaethyl-1,4,8,11-tetraazacyclotetradecane.

Preparation of Catalyst

The catalyst support is soaked in an aqueous solution of the mixture of silver salt and cyclic tetraamine which preferably contains 15–25% of an alcohol, e.g. ethanol, to give sufficient solubility for the amine. The aqueous solution normally contains from about 5 to about 20% by weight of the amine and from about 30 to 70% by weight of silver, present as a soluble silver salt, e.g. silver nitrate. If desired, small amounts, 0.001 to 1.0 percent, based on the weight of silver in the final catalyst, of a promoter can be added. Representative promoters include sodium oxide, calcium oxide, gold chloride, gold oxide, stannous oxide and particularly barium oxide. The promoters can be added as soluble salts which are convertible to oxides on heating in air and can be used individually or in any combination. Barium nitrate is a preferred source of the barium oxide. The volume of solution applied to the support should be about sufficient to be completely absorbed by the support material, in order to avoid the necessity of evaporating large amounts of solvent.

Following the absorption of the silver and amine compound, the catalyst is dried and then reduced by heating in the presence of a reducing gas, e.g., ethylene or propylene. The catalyst is then ready for use in the process for the oxidation of ethylene to ethylene oxide without further treatment. Drying is accomplished under vacuum by heating to a temperature of from 50° to 70° C while the temperature of reduction is from 150° to 250° C.

Alternatively, the solutions of silver salt and promoter and of the amine can be applied in separate steps from solutions of each, drying between steps. When applying separately, the order is immaterial, but it is preferred to employ the combination of ingredients from a single solution to avoid added processing steps.

Whatever method is employed for preparing the catalyst the resulting catalyst should, prior to reduction, contain about 0.5 to 2.0% of the amine and about 10 to 20% silver, based on the weight of support. After reduction, of course, the salt is converted to silver and the amine has been used up in the reduction or volatilized.

EXAMPLE 1

To prepare a supported silver catalyst in accordance with the invention 100 cc of 5/16-inch diameter alumina spheres were covered with an aqueous solution made by dissolving 1.0 g of HMTACD* in 70 ml. ethanol and adding this to 20 ml of aqueous solution of silver nitrate containing 12 g $AgNO_3$.

*5,7,7,12,14,14-hexamethyl-1,4,8,11-tetraazacyclotetradecane.

The entire solution and support were placed in a rotating flask and evaporated under a vacuum to assure uniform coating of the support. The dried catalyst was then reduced at 200° C under an ethylene atmosphere. The resulting catalyst contained 19.4% silver based on the total weight of the support and catalyst coating, or burden.

EXAMPLE 2

A large batch of catalyst for a pilot plant run was made by impregnating 6000 ml of 3/16-inch spheres of an alumina support. The solution was employed in the same manner as in the previous examples and contained 32 g HMTACTD*, 200 ml ethanol and 400 g of water. Drying was carried out employing a 3 cubic foot rotating conical vacuum dryer and the catalyst was reduced in ethylene at 190°-220° C. The catalyst contained 20 wt. % silver.

*5,7,7,12,14,14-hexamethyl-1,4,8,11-tetraazacyclotetradecane.

EXAMPLE 3

Example 2 was repeated except that only 21 g of HMTACTD* was used. The silver content was the same.

EXAMPLE 4

The catalysts prepared in Examples 1 and 2 were placed separately in a laboratory reactor consisting of a stainless steel tube 1½-inches (3.8 cm) in diameter, about 12-inches (30.5 cm) long heated by a heat transfer medium surrounding the tube and packed with 50 cc of catalyst. The feed gas, which had a mole % composition of 4-5% ethylene, 6% $O_2$, 8% $CO_2$ and the balance nitrogen, was passed through the reactor at a rate of 455 cc/min. at 210° C and 3 psig (0.211 kg/cm²).

A pilot plant reactor was also employed using a stainless steel tube 1½-inches (3.8 cm) in diameter and 20 feet (6.1 m) long filled with 4500 cc of catalyst. A feed stream, containing 4-5 mole % ethylene, 5-6 mole % oxygen, 7-8 mole % $CO_2$ and the balance nitrogen, was fed at the rate of 900 lbs/hr (408.2 kg/hr) at 250° C and 260 psig (9.28 kg/cm²).

The results of oxidizing ethylene over catalysts of the invention are shown in Table I. The temperatures, conversions and yields are all averages of at least three samples taken at various time intervals during a continuous run and have more significance than a single sample.

TABLE I

| Catalyst | Reactor | Temp. (° C) | $C_2H_4$ Conv. % | EO Yield % |
| --- | --- | --- | --- | --- |
| Example 2 | Pilot Plnt | 248 | 29.9 | 73.4 |
| Comp. Example A* | Pilot Plnt | 253 | 30.2 | 73.4 |
| Example 2 | Laboratory | 206.3 | 32.6 | 76.1 |
| Comp. Example B** | Laboratory | 214.5 | 31.3 | 66.4 |

*Comparative Example A employed a catalyst containing the same amount of silver but prepared according to Example 6 of U.S. 3,887,491.
**Comparative Example B employed a catalyst containing the same amount of silver, but employed no dispersing agent.

It should be noted that while the conversion and yield in the pilot plant runs (comparing the present catalyst with a good catalyst known to the art) are substantially the same, the present catalyst runs at a lower temperature than that of the art. Comparing the same catalyst of the present invention with one containing no dispersant shows a distinct advantage for the catalyst of the invention.

The catalyst of Example 1 was run in the laboratory reactor and several samples were taken during a run. The average temperature was 225° C which gave an average conversion of 30.4% and a yield of 73.3.

I claim:

1. In a process for making a supported silver catalyst in which soluble silver compound is impregnated onto a support from an aqueous solution thereof, subsequently dried and reduced to metallic silver, the improvement of adding to said aqueous solution a compound selected from the group of cyclic tetraamines having the formula

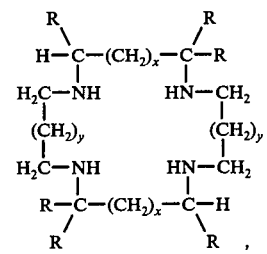

wherein x and y are independently selected integers of either 0 or 1 and R is methyl or ethyl, in an amount of from about 5 to about 20 percent by weight based on the weight of silver employed.

2. The process of claim 1 wherein the amount of silver salt employed is sufficient to provide 4-20 percent by weight silver based on the weight of finished catalyst.

3. The process of claim 2 in which a soluble metal salt convertible to the oxide on heating in air is employed as a promoter, said metal salt being selected from the group consisting of salts of barium, calcium, sodium, tin, and gold.

4. The process of claim 3 in which the metal salt is barium nitrate.

5. The process of claim 4 in which the cyclic tetraamine is 5,7,7,12,14,14-hexamethyl-1,4,8,11-tetraazacyclotetradecane.

* * * * *